(12) United States Patent
Dai et al.

(10) Patent No.: US 12,228,559 B2
(45) Date of Patent: Feb. 18, 2025

(54) BIOLOGICAL WATER-QUALITY DETECTION METHOD USING OBSTRUCTIVE MULTI-MODULE BIOLOGICAL WATER-QUALITY DETECTION DEVICE

(71) Applicants: CHINA THREE GORGES CORPORATION, Beijing (CN); HOHAI UNIVERSITY, Jiangsu (CN)

(72) Inventors: Huichao Dai, Beijing (CN); Jinqiao Mao, Jiangsu (CN); Gang Wang, Jiangsu (CN); Jiawei Xu, Jiangsu (CN)

(73) Assignees: CHINA THREE GORGES CORPORATION (CN); HOHAI UNIVERSITY (CN)

( * ) Notice: Subject to any disclaimer, the term of this patent is extended or adjusted under 35 U.S.C. 154(b) by 191 days.

(21) Appl. No.: 17/434,885

(22) PCT Filed: Mar. 1, 2021

(86) PCT No.: PCT/CN2021/078364
§ 371 (c)(1),
(2) Date: Aug. 30, 2021

(87) PCT Pub. No.: WO2021/208611
PCT Pub. Date: Oct. 21, 2021

(65) Prior Publication Data
US 2023/0046657 A1 Feb. 16, 2023

(30) Foreign Application Priority Data
Apr. 16, 2020 (CN) .......................... 202010299618.8

(51) Int. Cl.
*G01N 33/18* (2006.01)

(52) U.S. Cl.
CPC ..... *G01N 33/1866* (2013.01); *G01N 33/1893* (2013.01)

(58) Field of Classification Search
None
See application file for complete search history.

(56) References Cited

FOREIGN PATENT DOCUMENTS

| CN | 103105398 A | 5/2013 |
|----|-------------|--------|
| CN | 106680448 A | 5/2017 |

(Continued)

OTHER PUBLICATIONS

International Search Report of PCT/CN2021/078364.
Written Opinion of PCT/CN2021/078364.

*Primary Examiner* — David W Berke-Schlessel

(57) ABSTRACT

The invention discloses a biological water-quality detection method using said obstructive multi-module biological water-quality detection device. This device includes an obstruction index-selecting device and a water-quality testing device, wherein the obstruction index-selecting device is used to select a qualified or valid stepped obstruction level combination, the water-quality testing device detects the water-quality of the water body to be tested depending on the behavior at each obstruction in the valid obstruction level combination after injecting indicator organisms into the water body to be tested. The relationship between the degree of water pollution and the distribution area of indicator organisms is established and the distribution area of indicator organisms is counted in this method based on the difference between the behaviors of indicator organisms in the clean water body and the polluted water body count, so as to determine the degree of water pollution. The invention can accurately and quickly detect the degree of water body pollution, does not need the processes such as chemical analysis and physical detection, and has the advantages of low cost, fast operation and accurate results, etc.

9 Claims, 13 Drawing Sheets

(56) References Cited

FOREIGN PATENT DOCUMENTS

| | | | |
|---|---|---|---|
| CN | 110050730 | A | 7/2019 |
| CN | 110412230 | A | 11/2019 |
| CN | 111366700 | A | 7/2020 |
| JP | 2014178184 | A | 9/2014 | a top view of a flash a front view of a flash a schematic diagram of a flashing light in operation

BIOLOGICAL WATER-QUALITY DETECTION METHOD USING OBSTRUCTIVE MULTI-MODULE BIOLOGICAL WATER-QUALITY DETECTION DEVICE

TECHNICAL FIELD OF THE INVENTION

The invention relates to a biological water-quality detection method using an obstructive multi-module biological water-quality detection device.

DESCRIPTION OF THE PRIOR ART

The natural resources have been rapidly developed and utilized, with the rapid economic development and sharp population expansion. In the respect of water pollution, a large amount of industrial sewage and domestic wastewater are discharged into natural water, so water pollution problems have become increasingly extreme and severely threatens people's daily water safety. The conventional sewage-detecting method adopts chemical and physical component analysis, which can detect the specific pollution components and content in the water by means of chemical reaction, physical detection and other methods, but this detection has high cost, low efficiency, long time consumption, and time lag. Non-professionals cannot use these complicated sewage-detecting methods, and their use value is not so high as to timely get the result of water-quality.

In recent years, biological water pollution detection technology gradually grows up. For example, "water security on-line warning system and method based on avoidance behavior of aquatic organisms" with the publication number CN10119192, shows the behavior change signal of tested organisms by means of electrical signals obtained through multi-point monitoring, and realizes in-situ and real-time biological monitoring through the analysis and assessment to the electrical signals, further early warning against unknown pollutants in the water body. "A corridor-type water pollution warning device and warning method" with the publication number CN103105398A, uses a corridor with a grid, a video-capturing device, an image-recognizing system, etc. to convert the movement trajectory of fishes into digital image, and qualitatively measure whether the water-quality is polluted. These biological detection devices and methods directly and artificially designate a certain organism while selecting an indicator organism, but cannot measure whether the specified organism has the indicator effect and indicator accuracy, so there is a certain degree of blindness and some false alarms for them. But what is the most important is that there is currently no method and device that can achieve a system that can achieve selecting the indicator organism, obstruction indexes and monitoring indexes and finally evaluating results.

SUMMARY OF THE INVENTION

The invention aims to provide an obstructive multi-module biological water-quality detection device to solve the above-mentioned problems in the prior art.

The invention also aims to provide a biological water-quality detection method using the above obstructive multi-module biological water-quality detection device.

On the one hand, the invention provides an obstructive multi-module biological water-quality detection device. The obstructive multi-module biological water-quality detection device comprising a water-quality testing device, the water-quality testing device includes a testing water tank and three obstruction units, an inlet gate is installed at one end of the testing water tank, and an outlet gate is installed at the other end, the three obstruction units are arranged at the first, second and third sections inside the testing water tank, respectively, the distances from the first, second and third sections to the inlet gate increase in sequence, each obstruction unit includes an obstruction index-generating device and a counting device, the obstruction levels of the obstruction index-generating devices at the first, second, and third sections to the indicator organisms increases in sequence, the counting device is used to count the indicator organisms passing through said section.

Further, the obstruction index-generating device at the first section is used to generate a green single flash with frequency of 80-85 times/min, the obstruction index-generating device at the second section is used to generate a bubble curtain with air supply of 40-45 L/min, the obstruction index-generating device at the second section is used to generate a jet vortex with jet velocity of 1-1.1 m/s and a green single flash with frequency of 80-85 times/min.

Further, each obstruction unit further includes an warning device corresponding to and connected to the counting device.

Further, the obstruction index-generating device includes one or more combinations of a flashing light-generating device, a bubble curtain-generating device, a jet vortex-generating device, a temperature-controlling device, a sound-generating device.

Further, the testing water tank also includes a water-guiding pipe connected to the inlet gate and a water inlet of the testing water tank connected to the water-guiding pipe.

Further, also comprising an obstruction index-selecting device used to select each obstruction index-generating device, the obstruction index-selecting device includes a selection water tank, a pushing unit placed at one end of the selection water tank, and an obstruction-comparing unit and a monitoring unit that are placed at the other end of the selection water tank, the pushing unit is used to push the liquid in the selection water tank toward the obstruction unit, the obstruction-comparing unit includes a separating plate, the separating plate forms an obstruction section with four identical separated areas at the other end of selection water tank, and each separated area is used to install one or more kinds of obstruction index-generating devices, a water inlet is installed at one end of the selection water tank, a water outlet is installed on the other end, the monitoring unit is used to monitor the indicator organisms' behavior at the obstruction section.

Further, the pushing unit includes a pushing motor, a connecting chain rod and a pushing plate, the pushing motor drives the pushing plate through the connecting chain rod to push the liquid in the water tank to the other end.

Further, the monitoring unit includes two camera devices, and the two camera devices are located on both sides of the obstruction section, respectively.

On the other hand, the invention also provides a biological water-quality detection method using said obstructive multi-module biological water-quality detection device. The method includes the following steps:

S1: selecting an indicator organism, and selecting and installing the obstruction index-generating device required in each obstruction unit in the testing water tank, S2: injecting pollution-free water into the testing water tank, arranging the blocking net between the inlet gate and the obstruction unit at the first section, and placing the selected indicator organism between the blocking net and the inlet gate, adapting the selected indicator organism to the environment for m minutes, m≥10, S3: starting each obstruction index-generating device in the testing water tank, removing the blocking net so that the water body to be tested flows into the testing water tank through the inlet gate, S4: determining the water-quality of the water body to be tested according to the count changes of the counting devices inside the three obstruction units.

In S1, where the selecting the obstruction index-generating device required in each obstruction unit specially includes the following sub steps:

S11. establishing a single obstruction index, where the single obstruction index includes various single obstruction indexes, the single obstruction index can generate one or more kinds of obstruction levels, the single obstruction index includes any one of the following: a flash, a bubble curtain, a jet vortex, temperature, sound, etc., and establishing an indicator organism library, S12. selecting one indicator organism from the indicator organism library, and selecting at least three kinds of valid single obstruction levels from the single obstruction index database, where the method for selecting valid single obstruction levels is specifically as follows:

S121. selecting the obstruction level corresponding to one obstruction level from the single obstruction index database, and installing the single obstruction index-generating device capable of generating the corresponding obstruction level in the second, third, and fourth separated areas of the obstruction-comparing unit, respectively, no obstruction index-generating device in the first separated area, S122. filling the selection water tank with non-polluted water where indicator organisms are placed, pushing all the indicator organisms into the obstruction section by the pushing unit, counting the indicator organisms in each separated area by the monitoring unit, S123. marking the total number of selected indicator organisms as N, marking the number of the indicator organisms in the first to fourth separated areas as $N_a$, $N_b$, $N_c$, $N_d$, respectively, when $$N_a \geq \frac{2}{3}N,$$

the obstruction level corresponding to the selected single obstruction index having an obstructive effect on the indicator organism, which is called the valid single obstruction level, otherwise the invalid single obstruction level, having to select the obstruction level corresponding to the single obstruction index and make a judgement, if all the obstruction level of all the single obstruction indexes in the single obstruction index database are an invalid single obstruction level for the selected indicator organism, replacing the selected indicator organism so as to select a valid single obstruction level, S13. determining the obstruction index-generating device in the three obstruction units of the testing water tank according to at least three kinds of valid single obstruction levels selected in S12, where this step specifically includes the following sub steps:

S131. making three kinds of synthetical obstruction levels, where each synthetical obstruction level is any one or a combination of more of the above at least three kinds of valid single obstruction levels, installing the obstruction index-generating device generating the three kinds of synthetical obstruction levels in the second, third, and fourth separated areas of the obstruction section, respectively, no obstruction index-generating device in the first separated area, S132. filling the selection water tank with non-polluted water where indicator organisms are placed, pushing all the indicator organisms finally selected in S12 into the obstruction section by the pushing unit, counting the indicator organisms in each separated area by the monitoring unit, S133. when $N_a$, $N_b$, $N_c$, $N_d$ meets the following condition, judging that the selected three kinds of synthetical obstruction level combination is a valid synthetical obstruction level combination, otherwise an invalid synthetical obstruction level combination, having to repeat making new three kinds of synthetical obstruction level combination so as to finally select a valid synthetical obstruction level combination:

$$N_a = \frac{2}{3}N \pm 0.1N, \quad N_b = \frac{2}{9}N \pm 0.07N, \quad N_c = \frac{1}{12}N \pm 0.05N, \quad N_d = \frac{1}{36}N \pm 0.03N,$$

S14 installing an obstruction index-generating device at each section of the testing water tank to generate the valid synthetical obstruction level combination, where the obstruction index-generating device at the first section is used to generate the synthetical obstruction level corresponding to the second separated area in the valid synthetical obstruction level combination, the obstruction index-generating device at the second section is used to generate the synthetical obstruction level corresponding to the third separated area in the valid synthetical obstruction level combination, and the obstruction index-generating device at the third section is used to generate the synthetical obstruction level corresponding to the fourth separated area in the valid synthetical obstruction level combination, In S4, further comprising: in the case that the count of the counting device at the first section is less than 2/3 of the indicator organisms, the water-quality is normal; in the case that the count of the counting device at the first section is not less than 2/3 of the indicator organisms and the count of the counting device at the second section is less than 2/3 of the indicator organisms, the water-quality is slightly polluted; in the case that the count of the counting device at the second section is not less than 2/3 of the indicator organisms and the count of the counting device at the third section is less than 2/3 of the indicator organisms, the water-quality is moderately polluted; in the case that the count of said counting device at the third section is not less than 2/3 of the indicator organisms, the water-quality is heavily polluted.

Compared with the prior art, the invention has the following advantages:

1. There is no need to analyze the physical and chemical components for water-quality and use the image-recognizing system and other complicated systems, and no need to calculate the indexes such as indicator organisms' swimming trajectory, swimming speed, and the like, which overcomes the time lag of conventional detection devices. Different levels of constraints are imposed on the avoidance behavior of indicator organisms to polluted water, and amplify the indicator organisms' avoidance behavior to different degrees of polluted water (slight pollution, moderate pollution, heavy pollution), by using three obstruction states of low obstruction state, medium obstruction state and high obstruction state, so we can visually detect whether the water body is polluted, accurately and quickly evaluate the degree of water body pollution, and monitor the water body pollution status in real time.
2. The range of the PH value of the water body to be tested can be roughly estimated.
3. In the respect of selecting indicator organisms, obstruction indexes and monitoring indexes, and finally evaluating results, a complete obstructive multi-module biological water-quality detection method and a device thereof have been put forward.
4. The invention has simple structure, low cost, intuitiveness for observation, powerful function, and possibility to correctly operate even for non-professionals, so it can be applied to rapid water-quality detection of water body such as lakes, reservoirs, rivers, and domestic sewage.

DETAILED DESCRIPTION OF THE INVENTION

In order to make the invention clearer, the invention is further described as follows in detail in conjunction with specific examples and with reference to the figures.

As shown in FIGS. 2-5, the invention provides an obstructive multi-module biological water-quality detection device, which includes an obstruction index-selecting device and a water-quality testing device, wherein the obstruction index-selecting device is used to select a qualified or valid stepped obstruction level combination, the water-quality testing module detects the water-quality of the water body to be tested depending on the behavior at each obstruction in the valid obstruction level combination after injecting indicator organisms into the water body to be tested.

Figure 2:
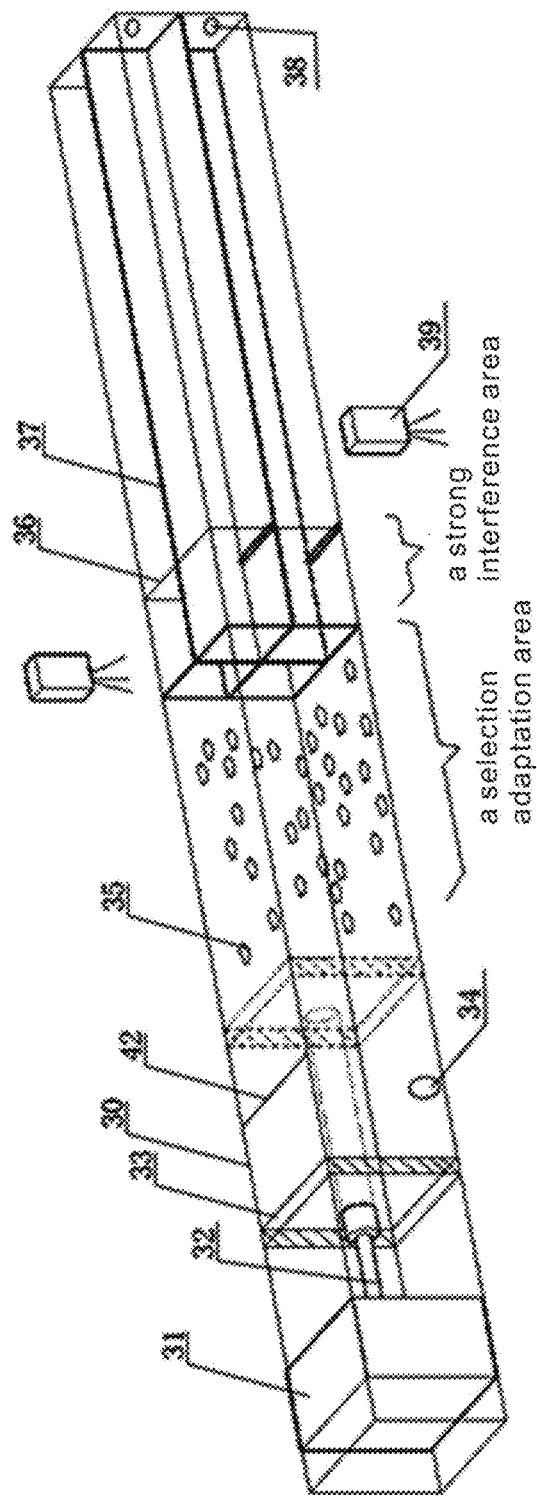
FIG. 2 is a schematic diagram of the index-selection water tank used in the invention.
Figure 3:
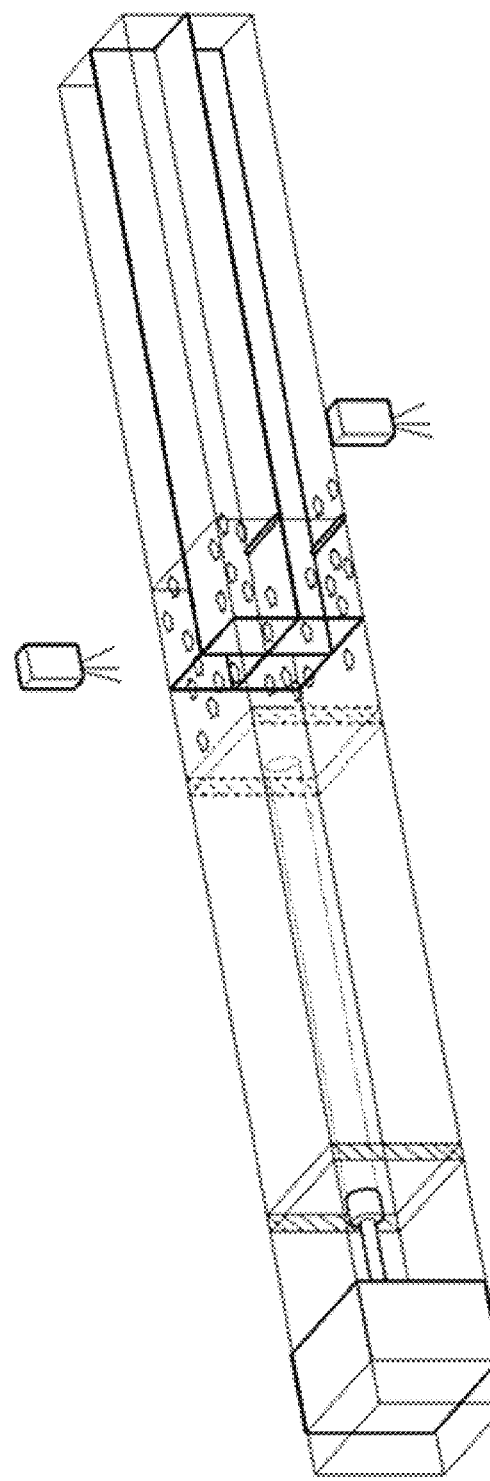
FIG. 3 is a schematic diagram of the operation state of the selection water tank.
Figure 4:
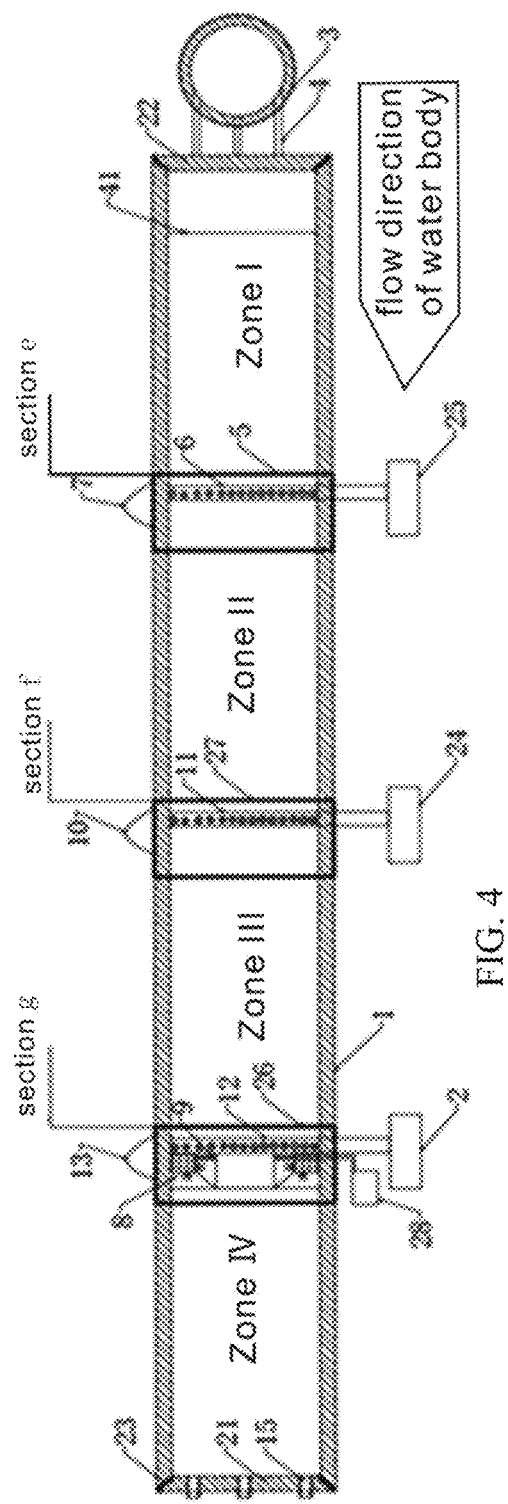
FIG. 4 is a plan view of the testing water tank used in the invention.
Figure 5:
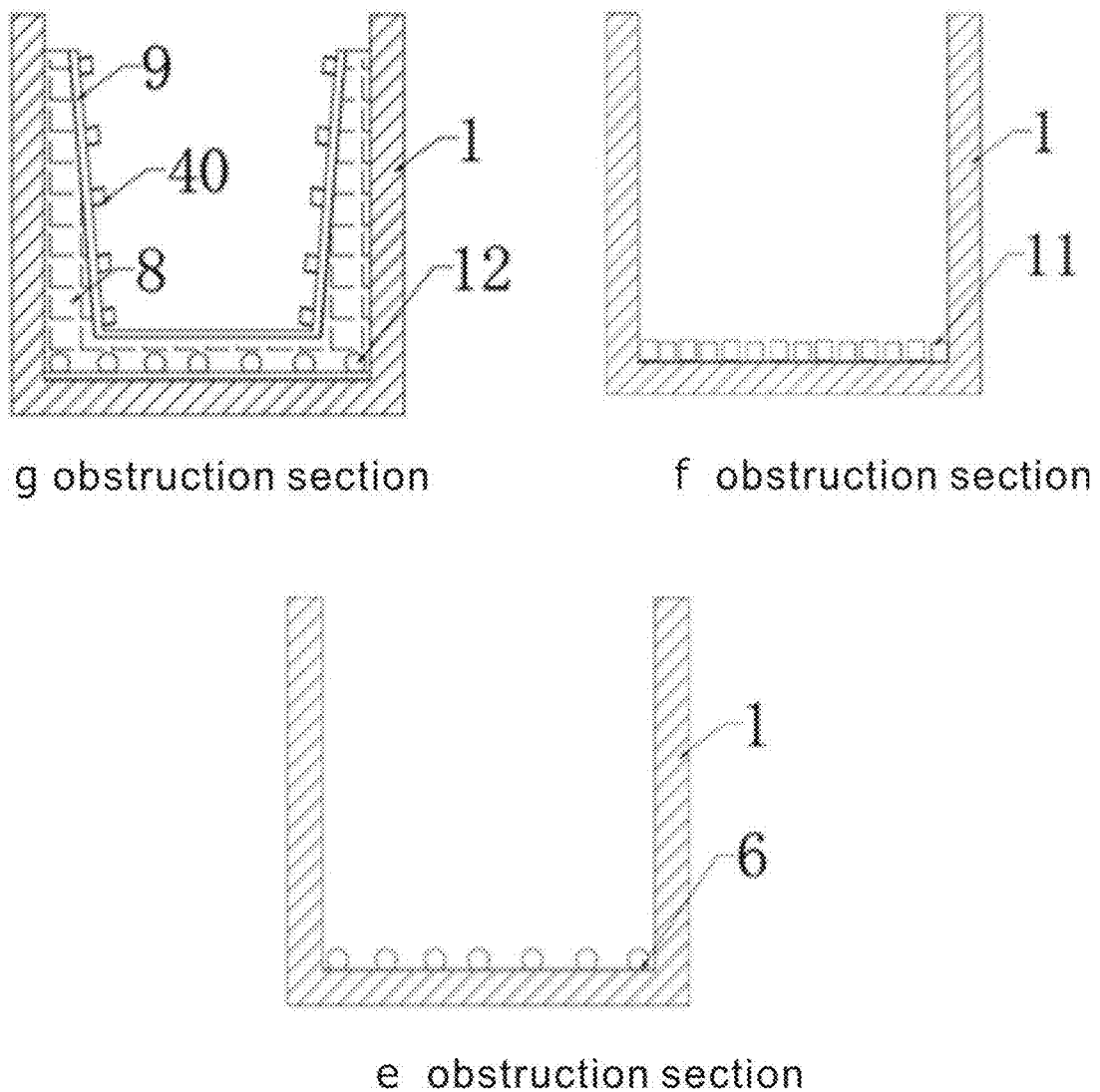
FIG. 5 is a cross-sectional view of the obstruction unit at the three sections in FIG. 4.

The obstruction index-selecting device includes a selection water tank 30, a pushing unit placed at one end of the selection water tank 30 (see the left end of FIGS. 2 and 3), and an obstruction-comparing unit and a monitoring unit that are placed at the other end of the selection water tank 30 (see the right end of FIGS. 2 and 3). The pushing unit is used to push the liquid in the selection water tank 30 to the obstruction unit. The obstruction-comparing unit includes a separating plate, and the separating plate forms an obstruction section with four identical separated areas at the other end of the selection water tank 30, and each separated area is used to install a different obstruction index-generating device. A water inlet 34 is installed at the left end of the selection water tank 30, can replenish water into the selection water tank 30; a water outlet 38 is installed on the right end of the selection water tank 30, can discharge the water in the selection water tank 30. The monitoring unit is used to monitor the indicator organisms' behavior at the obstruction section.

The pushing unit includes a pushing motor 31, a connecting chain rod 32 and a pushing plate 33. The pushing motor 31 is connected to the pushing plate 33 through the connecting chain rod 32, after staring the pushing motor 31, the pushing plate 33 can be pushed to move in the direction close to the obstruction-comparing unit. The area from the pushing plate 33 in the selection water tank 30 to the obstruction section 36 is a selection adaptation area, and the area near the obstruction section 36 is a strong interference area. The obstruction section 36 is divided into four areas a, b, c, d by the separating plate 37, and the obstruction-generating device are all installed in the four areas a, b, c, d, can generate corresponding an obstruction index, and the water outlets 38 are installed in the four areas a, b, c, d. The monitoring unit includes two camera devices, and the two camera devices 39 are located on both sides of the obstruction section 36, respectively.

The water-quality testing device includes a testing water tank 1 and three obstruction units. An inlet gate 22 is installed at one end of the testing water tank 1 (see the right end of FIG. 4), and an outlet gate 21 is installed at the other end (see the left end of FIG. 4). The three obstruction units are respectively arranged at the sections e, f, and g inside the testing water tank 1. As shown in FIG. 3, the distances from the sections e, f, and g to the inlet gate gradually increase. As shown in FIGS. 2 and 3, the testing water tank 1 is divided into four areas I, II, III, and IV by three obstruction sections e, f, and g. The inlet gate 22 and the outlet gate 21 are connected with the testing water tank 1 through a gate groove 23 on the testing water tank 1, and the water inlet 3 of the testing water tank is connected with the inlet gate 22 through a water-guiding pipe 4. Each obstruction unit includes an obstruction index-generating device and a counting device, and also includes an warning device corresponding to and connected to the counting device one-to-one. The obstruction index-generating device at each obstruction unit is selected from one or more combinations of a flashing light-generating device, a bubble curtain-generating device, a jet vortex-generating device, a temperature-controlling device, a sound-generating device, which can be selected based on the obstruction index-selecting device described above. The counting device is used to count the indicator organisms passing through the section.

Based on the obstructive multi-module biological water-quality detection device shown in FIGS. 2-5, the invention also provides a biological water-quality detection method using the above obstructive multi-module biological water-quality detection device. The method includes the following steps:

S1: Selecting an indicator organism, and selecting and installing the obstruction index-generating device required in each obstruction unit in the testing water tank 1.

S2: Injecting pollution-free water into the testing water tank 1, arranging the blocking net 41 between the inlet gate 22 and the obstruction unit at the first section, and placing the selected indicator organism between the blocking net 41 and the inlet gate 22, adapting the selected indicator organism to the environment for m minutes, m≥10.

S3: Starting each obstruction index-generating device in the testing water tank 1, removing the blocking net so that the water body to be tested flows into the testing water tank 1 through the inlet gate 22.

S4: Determining the water-quality of the water body to be tested according to the count changes of the counting devices inside the three obstruction units.

Figure 1:
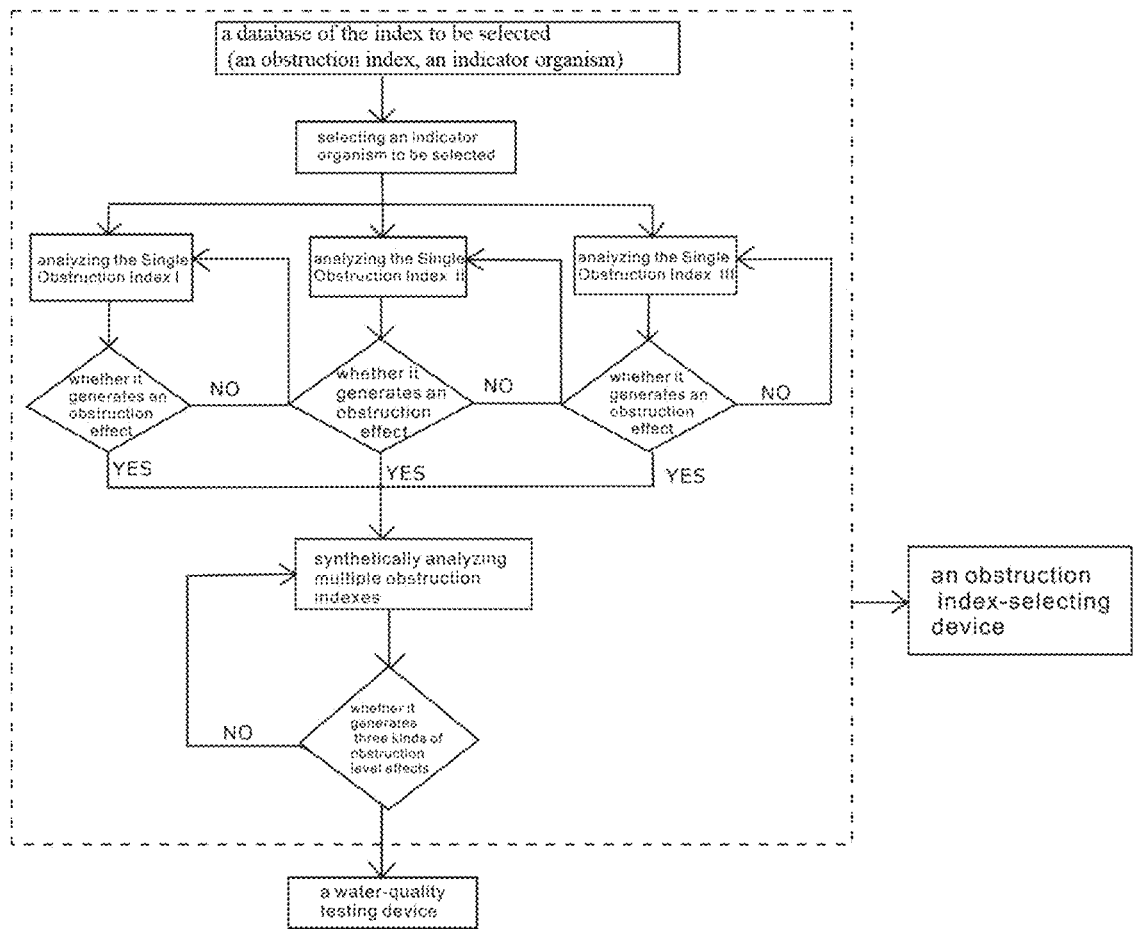
FIG. 1 is a schematic flow chart diagram of an obstructive multi-module biological water-quality detection method according to the invention.

The process of S1 is roughly shown in FIG. 1, specifically includes the following sub steps:

S11: Establishing a database of the index to be selected.

(S111) Establishing a single obstruction index database, which can include, but is not limited to the index to be selected such as flashing light, a bubble curtain, a jet vortex, temperature, sound. The technology using a bubble curtain and flashing light to expel fishes is one of the important potential non-damaging fish-expelling technologies, and the bubble curtain and flashing light function as obstruction to the specific organism. The direction of jet flow is perpendicular to the direction of the water flow, which will have a certain initial velocity at the outlet through a pressure water pipe. The speed difference and viscosity between the static water body and the jet flow are used to generate a vortex with vorticity in the water body, thereby forming the jet vortex. The jet vortex will influence on the sensory system of indicator organisms such as the vision and hearing to a certain extent, so it is also a potential obstruction index.

Each single obstruction index also has one or more kinds of corresponding obstruction levels, so-called obstruction level is characterized by the attribute and intensity value of a certain single obstruction index, for example, the color of, frequency and intensity value of flashing light, and density of a bubble curtain, vortex of a jet vortex, temperature value, volume value, etc.

(S112) Establishing an indicator organism library, in which the selected indicator organism should have the characteristics such as fast movement and sensitive response to environmental changes. The indicator organism library may include, but is not limited to, fishes living in upper-middle water, amphibious frogs, benthic eels, etc. In this embodiment, the indicator organism library contains a light spinibarbus fish, a carp, a silver carp, and an eel.

S12: Selecting one kind of indicator organism from the indicator organism library, and selecting at least three kinds of valid single obstruction levels from the single obstruction index database.

For example, the light spinibarbus fishes are selected as the preliminary indicator organism, with their number of 100, have body length of (10±1) cm and body weight of (12±1) grams, and are juvenile fish.

Figure 8:
FIG. 8 is a schematic diagram of a flashing light in operation.
Figure 8:
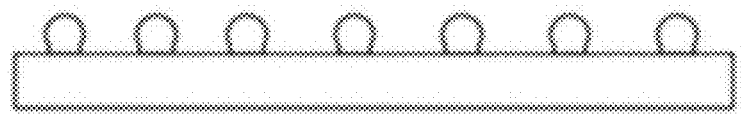
Figure 8:
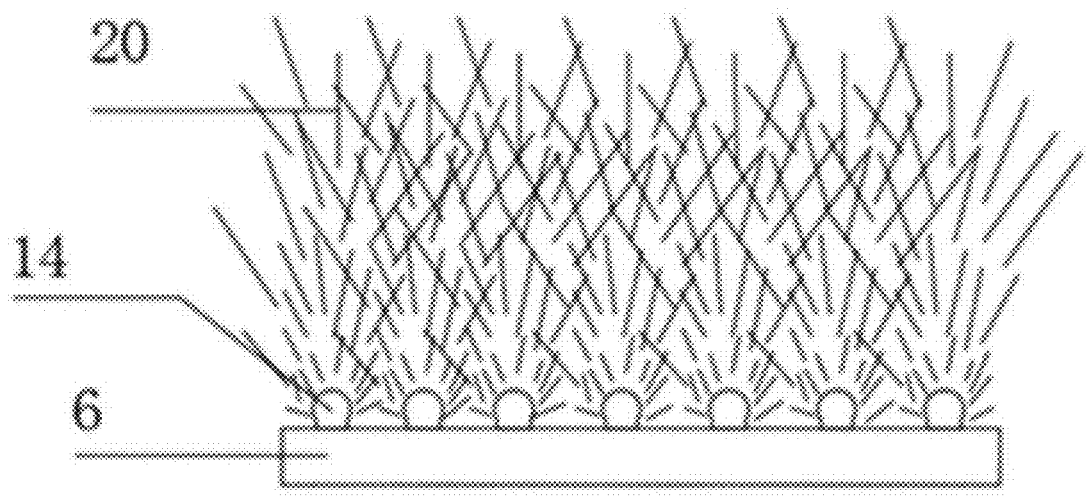

The specific method for selecting the valid single obstruction level is as follows:

(S121) Selecting a jet vortex from the single obstruction index database as the preliminary single obstruction level, and preliminarily setting up the single obstruction level of the jet vortex to jet velocity of 1-1.11 m/s, as shown in FIG. 8. The obstruction index-generating devices capable of generating jet vortices with jet velocity of 1-1.1 m/s are installed in the second, third, and fourth separated areas of the obstruction section 36 (corresponding to Area b, c, d in FIG. 9, respectively), respectively, and no obstruction index-generating device is installed in the first separated area (corresponding to Area a in FIG. 9).

Figure 9A:
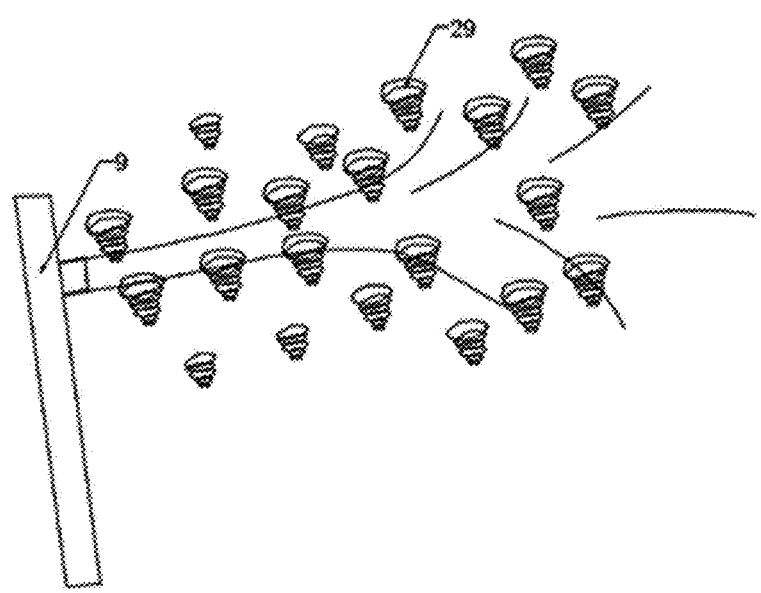
FIGS. 9(a) and 9(b) are a side view and a top view of the working diagram of a jet vortex, respectively.
Figure 9B:
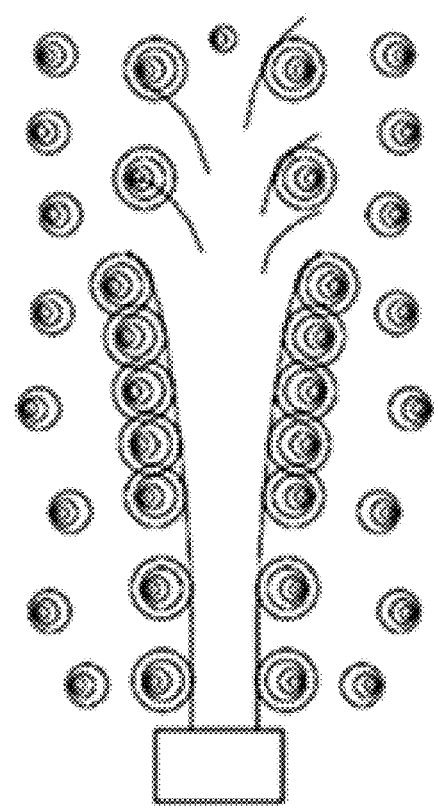

(S122) Filling an obstruction index-selection water tank 30 with clean and pollution-free water. In this embodiment, the obstruction index-selection water tank 30 is a single-layer transparent glass water tank shaped as a rectangular parallelepiped (the length, width and height are 26 m×1 m×1.5 m in inner dimension, the length, width, and height are 26 m×1.2 m×1.7 m in outer dimension). We put a blocking net 42 in the selection adaptation area, (that is, between the pushing plate 33 and the obstruction section 36) of the obstruction index-selection water tank 30, and put 100 light spinibarbus fishes into the area between the blocking net 42 and the pushing plate 33 to keep adapting the light spinibarbus fishes to the water environment for 30 minutes. We start a water pump to generate a jet vortex on the obstruction section 36, remove the blocking net 42, start the camera device 39 and a pushing motor 31 to expel the 100 light spinibarbus fishes forward until they enter the strong interference area near the obstruction section 36 (as shown in FIGS. 2, 3 and 9). We use a monitoring unit at the obstruction section 36 to count the number of indicator organisms in each separated area.

(S123) Analyzing the light spinibarbus fishes in the four areas of a, b, c, d, marking the total number of selected indicator organisms as N, marking the number of the indicator organisms in the separated areas I-IV as $N_a$, $N_b$, $N_c$, $N_d$, respectively, when $N_a \geq 2/3N$, the obstruction level corresponding to the selected single obstruction index has an obstructive effect on the indicator organism, which is called the valid single obstruction level, otherwise it is the invalid single obstruction level, so we have to select the obstruction level corresponding to the single obstruction index again and make a judgement. If all the obstruction level of all the single obstruction indexes in the single obstruction index database are an invalid single obstruction level for the selected indicator organism, the selected indicator organism is replaced so as to select a valid single obstruction level. In this embodiment, since the numbers of the light spinibarbus fishes in the four areas a, b, c, d are: 75, 8, 10, 7, respectively, we judge that the jet vortex index selected in this embodiment with jet velocity of 1-1.1 m/s meets the requirements, according to the obtained number of the light spinibarbus fishes in each area.

We replace the obstruction index, jet vortex with other indexes in the single obstruction index database, and do not make a judgement again until at least three kinds of valid single obstruction levels have been selected. In this embodiment, we finally select the light spinibarbus fish as the indicator organism that meets the relevant requirements of the single obstruction index analysis module, its valid single obstruction level is: green single flash with frequency of 80-85 times/min, low-density bubble curtain with air supply of 40-45 L/min, high-density bubble curtain with air supply of 75-80 L/min, and jet vortex with jet velocity of 1-1.1 m/s.

Figure 10:
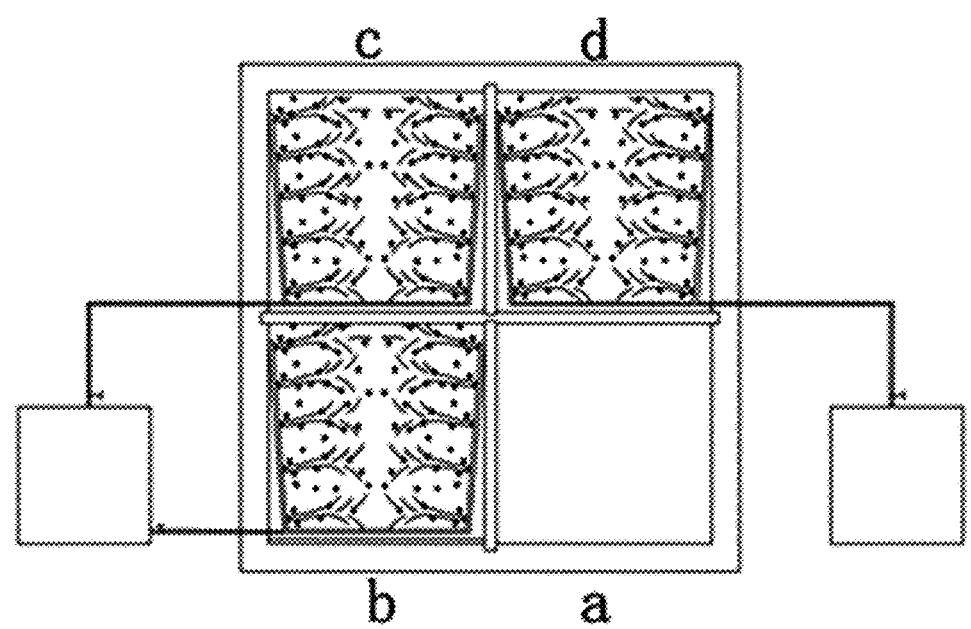
FIG. 10 is a schematic diagram of the obstruction section in the selection water tank when selecting a valid single obstruction index.
Figure 11:
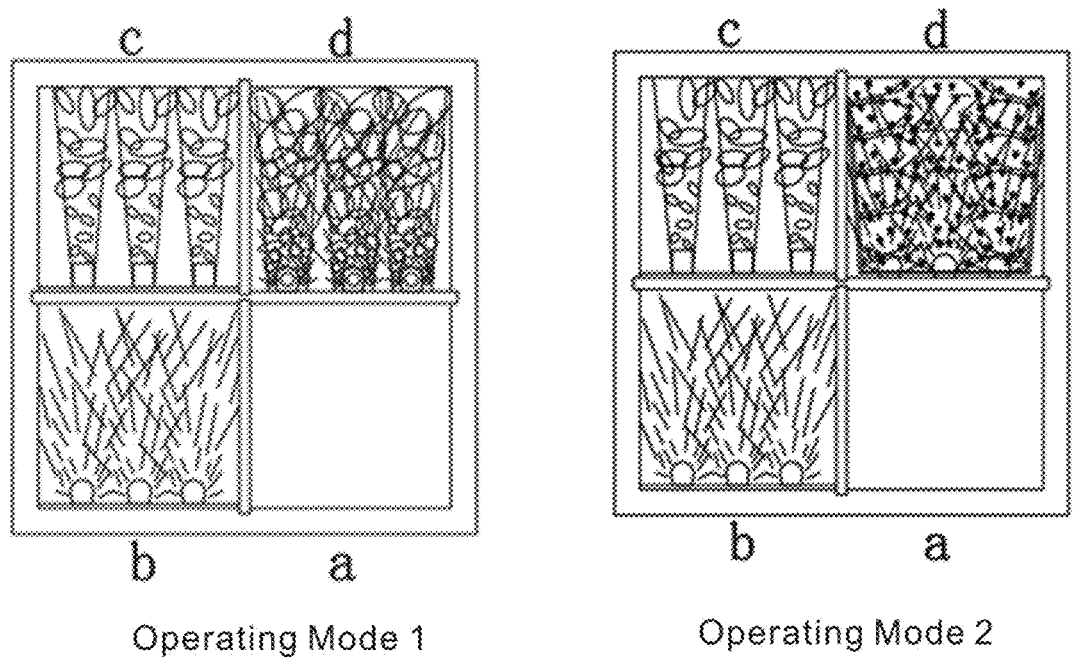
FIG. 11 is a schematic diagram of the obstruction section in the selection water tank when selecting an invalid synthetical obstruction index combination.

S13: Determining the obstruction index-generating device in the three obstruction units of the testing water tank 1 according to the four kinds of valid single obstruction levels selected in S12, this step specifically includes the following sub steps:

S131: Combining the four kinds of valid single obstruction levels selected in S12 to make three kinds of synthetical obstruction levels, among which each synthetical obstruction level is any one or a combination of more of the above four kinds of valid single obstruction levels. For example, FIG. 10 shows two sets of the synthetical obstruction level combination to be selected, corresponding to the following combination of the Operating Mode 1 and the Operating Mode 2, respectively. Operating Mode 1: Zone a presents blank control, Zone b presents flashing light (single flashing light, white, frequency of 60-65 times/min), Zone c presents a low-density bubble curtain (air supply of 40-45 L/min), Zone d presents a high-density bubble curtain+flashing light (air supply of 75-80 L/min, single flashing light, white, frequency of 80-85 times/min).

Operating Mode 2: Zone a presents blank control, Zone b presents flashing light (single flashing light, green, frequency of 80-85 times/min), Zone c presents a low-density bubble curtain (air supply of 40-45 L/min), Zone d presents a jet vortex+flashing light (jet velocity of 1-1.1 m/s, single flashing light, green, frequency of 80-85 times/min).

S132: Filling the selection water tank 30 with clean water, putting 100 light spinibarbus fishes into the area between the blocking net 41 and the pushing plate 33 to keep adapting the light spinibarbus fishes to the water environment for 30 minutes. We start the corresponding obstruction-generating device to generate the synthetical obstruction level combination presented in the Operating Mode 1 and the Operating Mode 2, remove the blocking net 42, start the camera deice 39 and a pushing motor 31 to expel the 100 light spinibarbus fishes forward until they enter the strong interference area near the obstruction section 36.

S133: Analyzing the light spinibarbus fishes in the four areas a, b, c, d at the obstruction section 36. In the case of the synthetical obstruction index combination corresponding to the Operating Mode 1 in FIG. 10, the numbers of the light spinibarbus fishes $N_a$, $N_b$, $N_c$, $N_d$ in the four areas a, b, c, d are 61, 17, 10, 12, respectively, as the numbers of the light spinibarbus fishes do not meet $$N_a = \frac{2}{3}N \pm 0.1N, \ N_b = \frac{2}{9}N \pm 0.07N, \ N_c = \frac{1}{12}N \pm 0.05N, \ N_d = \frac{1}{36}N \pm 0.03N,$$

according to the every zone, we judge that the three kinds of synthetical obstruction level combination selected for the Operating Mode 1 is an invalid synthetical obstruction level combination. In the case of the synthetical obstruction index combination corresponding to the Operating Mode 2, the numbers of the light spinibarbus fishes $N_a$ $N_b$, $N_c$, $N_d$ in the four areas a, b, c, d are 75, 16, 6, 3, respectively, meet $$N_a = \frac{2}{3}N \pm 0.1N, \ N_b = \frac{2}{9}N \pm 0.07N, \ N_c = \frac{1}{12}N \pm 0.05N, \ N_d = \frac{1}{36}N \pm 0.03N,$$

so we judge that the three kinds of synthetical obstruction level combination selected for the Operating Mode 2 is an valid synthetical obstruction level combination.

S14: installing an obstruction index-generating device at each section of the testing water tank 1 to generate the valid synthetical obstruction level combination corresponding to the Operating Mode 2 determined in S13.

Figure 6A:
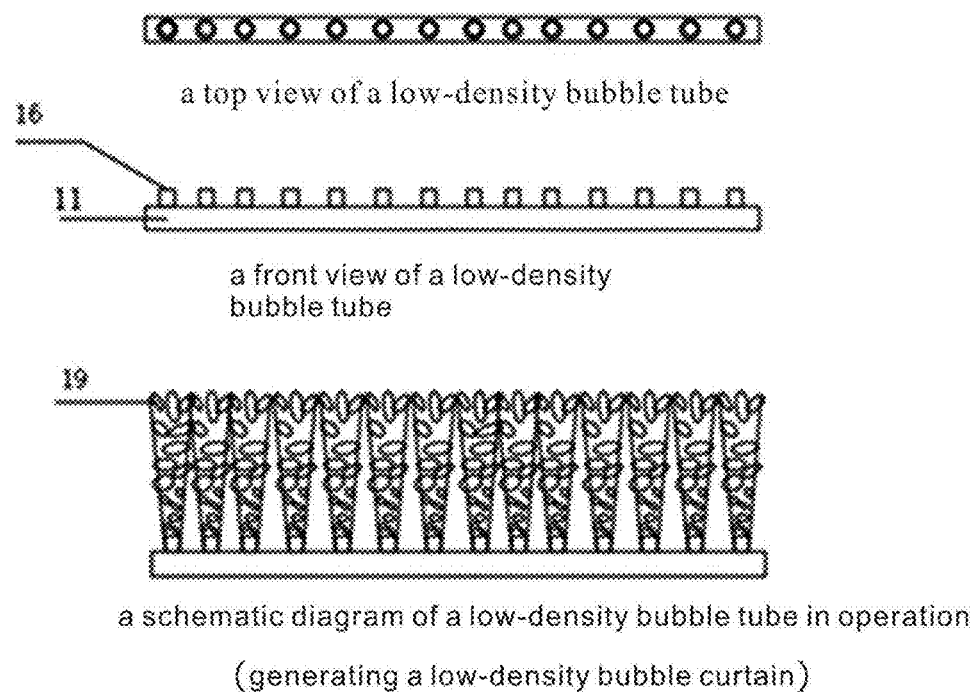
FIGS. 6(a) and 6(b) are a schematic diagram of a low-density bubble tube and a schematic diagram of a high-density bubble tube, respectively.
Figure 6B:
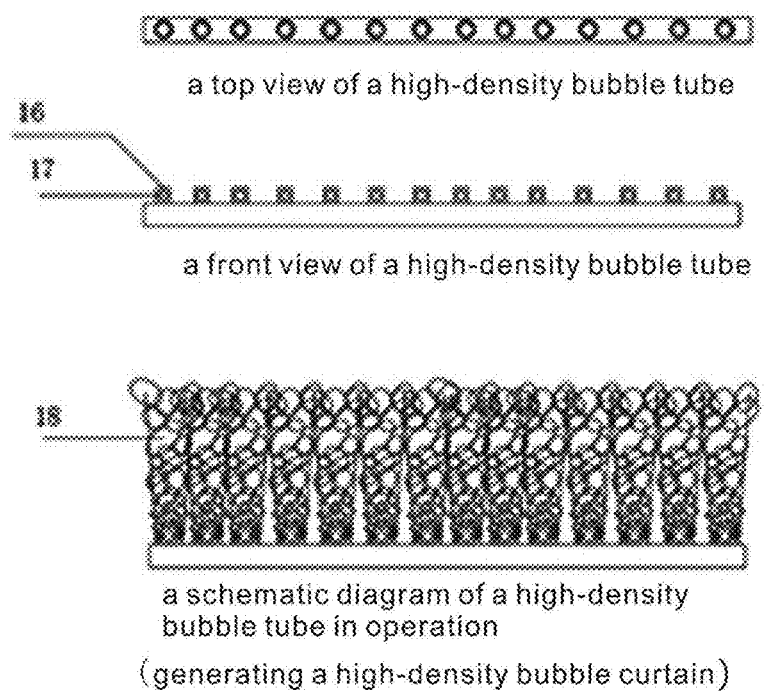
Figure 7:
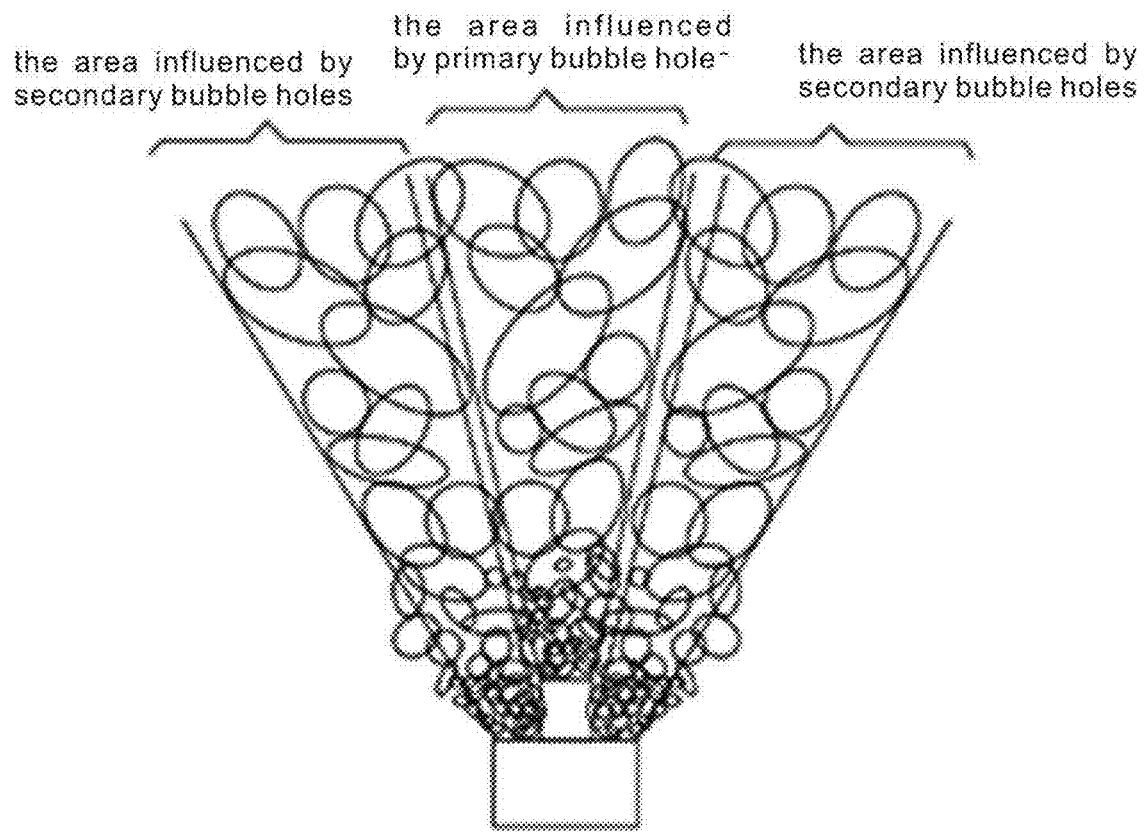
FIG. 7 is a side view of bubble-generating 3D diagram.

In this embodiment, the testing water tank 1 uses a "⌴" shaped concrete uncovered water tank (the length, width and height are 26 m×1 m×1.5 m in inner dimension, the length, width, and height are 26 m×1.2 m×1.7 m in outer dimension). As shown in FIG. 6-8, correspondingly, the obstruction index-generating device at the section e of the testing water tank 1 includes a first flash belt 6 and a first power source 25, the obstruction index-generating device at the section f includes a low-density bubble tube 11 and an air pump 24, and the obstruction index-generating device at the section g includes a jet-separating pier 8, a jet tube 9, a high-density bubble tube, a pressure water pump 28, a second flash belt 12, and a second power source 2. Among them, the first flash belt 6, the low-density bubble tube 11, and the second flash belt 12 are all installed on the bottom surface of the testing water tank 1, the jet-separating pier 8 is installed inside the testing water tank 1, and the jet tube 9 is embedded and installed inside the jet-separating pier 8, a jet nozzle 40 is installed on the jet tube 9. The counting devices 5, 26 and 27 at the sections e, f, and g are all infrared counting devices, which are all installed on the upper part of the corresponding three obstruction sections. 14 primary bubble holes 16 without secondary holes on the side are installed on the low-density bubble tube 11, and 14 primary bubble holes 16 and 56 secondary bubble holes 17 are concurrently installed on the high-density bubble tube. The air pump 24 supplies compressed air to the low-density bubble tube 11 and the high-density bubble tube. When intending to generate low-density bubbles, the air supply of the air pump 24 is controlled at 40 L-45 L/min to generate the low-density bubble curtain 19; when intending to generate high-density bubbles, the air supply of the air pump 24 is controlled at 75 L-80 L/min to generate the high-density bubble curtain 18. The diameter of the primary bubble hole 16 is 0.5 cm, and the diameter of the secondary bubble hole 17 is 0.3 cm. The first power source 25 supplies electricity to the first flash belt 6, and the second power source 2 supplies electricity to the second flash belt 12, and the flash 14 is installed on the first flash belt 6 and the second flash belt 12. The flash 14 produces a single flashing light 20, the color and frequency of the single flashing light 20 are controllable, and the frequency is 60-100 times per minute. The pressure water pump 28 provides the jet pipe 9 with pressurized water flow. The water pump 28 is an RGZ15-20 booster pump, which can provide the jet nozzle 40 with a pressurized flow of 1-3 m/s.

S2 specifically includes: injecting clean water into the water-quality-testing water tank 1, so as to make the water-quality-testing water tank 1 filled with clean water, then putting 100 light spinibarbus fishes into the area between the blocking net 41 and the inlet gate 22 to keep adapting the light spinibarbus fishes to the clean water environment for 30 minutes.

S3 specifically includes: starting the obstruction-generating power device of the obstruction section e, f, g in the testing water tank 1 to generate flashing light on the obstruction section e (single flashing light, green, frequency of 80-85 times/min), and a low-density bubble curtain on the obstruction section f (air supply of 40-45 L/min), a jet vortex and a flashing light on the obstructing section g (jet velocity of 1-1.1 m/s, single flashing light, green, frequency of 80-85 times/minute), removing the blocking net 41, quickly pouring 10 L of the water to be tested into the cylindrical water inlet 3 to make the water to be tested into the testing water tank 1 through the inlet gate 22, and keep it for 5 minutes.

In S4, determining the water-quality of the water body to be tested includes the following sub steps:

S41: In pollution-free situation, when the added water body to be tested is not polluted, the indicator organisms gather at Zone I in the water tank, moving about, under the action of the obstruction index, according to the selected indicator organism's own biological habits, no less than 2/3 of the indicator organisms continuously exist at Zone I, so the slight pollution warning lamp 7 will not light up, indicating that the water-quality of the water body to be tested is normal and not polluted.

S42: In slight pollution situation, in the case that the added water body to be tested is slightly polluted, when the water body to be tested enters the water-quality-testing tank through the water-guiding pipe, the water body slightly polluted gradually spreads forward, so the indicator organisms suddenly make their swimming behavior active according to the selected indicator organism's own biological habits, and raise the indexes such as moving speed, breathing rate, in order to avoid the water body slightly polluted from spreading and invading, the indicator organisms try to pass through the low-level obstruction section. When more than 2/3 of the indicator organisms pass through the low-level obstruction section, the slight pollution warning lamp 7 lights up to give an alarm, after the fish groups passed through the low-level obstruction section, they enter Zone II of the water-quality-testing water tank. As the obstructive effect of the moderate-level obstruction section is stronger than that of the low-level obstruction section, the tested fishes will not easily try to pass the moderate-level obstruction section under the threat of the intrusion only by the water body slightly polluted. No less than 2/3 of the indicator organisms choose to adapt to the water environment and continuously exist at Zone II of the water-quality-testing water tank. The moderate pollution warning lamp 10 does not light up, while only the slight pollution warning lamp 7 lights up, so we judge that the water body is slightly polluted.

S43: In moderate pollution situation, in the case that the added water body to be tested is moderately polluted, in order to avoid polluted water and protect themselves, the indicator organisms first pass through the low-level obstruction section according to the selected indicator organism's own biological habits, then the slight pollution warning lamp 7 lights up. The indicator organism chooses to try to pass through the moderate-level obstruction section under the invasion of the water body moderately polluted, when 2/3 of indicator organisms pass through the moderate-level obstruction section, the moderate pollution warning lamp 10 lights up. After the indicator organisms passed through the moderate-level obstruction section, they enter Zone III of the water-quality-testing water tank. As the obstructive effect of the high-level obstruction section is stronger than that of the moderate-level obstruction section, the indicator organisms will not easily try to pass the high-level obstruction section under the threat of the intrusion by the water body moderately polluted. The indicator organisms choose to adapt to the water environment, and no less than 2/3 of the indicator organisms continuously exist at Zone III of the water-quality-testing water tank. The heavy pollution warning lamp 13 does not light up, while the moderate pollution warning lamp 10 lights up, so we judge that the water body is moderately polluted.

S44: In heavy pollution situation, in the case that the added water body to be tested is heavily polluted, the indicator organism stays continuously excited according to the selected indicator organism's own biological habits, and they sequentially pass through the low-level obstruction section and the moderate-level obstruction section. Both the slight pollution warning lamp 7 and the moderate pollution warning lamp 10 light up, right now, the indicator organisms enter Zone III. The fish groups attempt to pass through the high-level obstruction section, severely threatened by the water body heavily polluted, and eventually more than 2/3 of the indicator organisms enter Zone IV of the water-quality-testing water tank, and the heavy pollution warning lamp 13 lights up, so we judge that the water body is heavily polluted.

According to the different pollution degree of the water body to be tested, the results of some test examples are shown in Table 1-5. Among them, "o" means that the warning lamp gives no alarm, and "√" means that the warning lamp gives an alarm. Among them, when the water-quality of the water body to be tested is verified by physical and chemical testing methods, the PH value is used to measure the degree of water pollution (6.5<PH<7.8 means normal water-quality; 5<PH<6.5 or 7.8<PH<8.5 means slight pollution; 3<PH<5 or 8.5<PH<9 means moderate pollution; PH<3 or 9<PH means heavy pollution). In different circumstances, the operator can choose a measurement index and a measurement standard by himself according to the actual situation, which are not limited to the index and standard proposed in this example.

TABLE 1

Test Example I

| Test Method | Distribution number of tested fishes in each zone | | | | | Indicator light situation | | | Test result | |
| --- | --- | --- | --- | --- | --- | --- | --- | --- | --- | --- |
| | Zone I | Zone II | Zone III | Zone IV | Dead | Slight pollution warning lamp | Moderate pollution warning lamp | heavy pollution warning lamp | | |
| biological detection | 95 | 5 | 0 | 0 | 0 | o | o | o | Normal water-quality | The test results are consistent |
| physical and chemical analysis | pH: 7.2 chemical oxygen demand (COD): 14 mg/l | | | | | ammonia-nitrogen ($NH_3$—N): 0.12 mg/l faecal coliform: 187 pcs/L | | | Normal water-quality | |

TABLE 2

Test Example II

| Test Method | Distribution number of tested fishes in each zone | | | | | Indicator light situation | | | Test result | |
| --- | --- | --- | --- | --- | --- | --- | --- | --- | --- | --- |
| | Zone I | Zone II | Zone III | Zone IV | Dead | Slight pollution warning lamp | Moderate pollution warning lamp | heavy pollution warning lamp | | |
| biological detection | 0 | 0 | 8 | 84 | 8 | ✓ | ✓ | ✓ | heavy pollution | The test results are consistent |
| physical and chemical analysis | pH: 9.4 chemical oxygen demand (COD): 38 mg/l | | | | | ammonia-nitrogen ($NH_3$—N): 1.7 mg/l faecal coliform: 19850 pcs/L | | | heavy pollution | |

TABLE 3

Test Example III

| Test Method | Distribution number of tested fishes in each zone | | | | | Indicator light situation | | | Test result | |
| --- | --- | --- | --- | --- | --- | --- | --- | --- | --- | --- |
| | Zone I | Zone II | Zone III | Zone IV | Dead | Slight pollution warning lamp | Moderate pollution warning lamp | heavy pollution warning lamp | | |
| biological detection | 0 | 12 | 76 | 8 | 4 | ✓ | ✓ | ○ | moderate pollution | The test results are consistent |
| physical and chemical analysis | pH: 4.7 chemical oxygen demand (COD): 18 mg/l | | | | | ammonia-nitrogen ($NH_3$—N): 0.82 mg/l faecal coliform: 10253 pcs/L | | | moderate pollution | |

TABLE 4

Test Example IV

| Test Method | Distribution number of tested fishes in each zone | | | | | Indicator light situation | | | Test result | |
| --- | --- | --- | --- | --- | --- | --- | --- | --- | --- | --- |
| | Zone I | Zone II | Zone III | Zone IV | Dead | Slight pollution warning lamp | Moderate pollution warning lamp | heavy pollution warning lamp | | |
| biological detection | 0 | 10 | 86 | 2 | 2 | ✓ | ✓ | ○ | moderate pollution | The test results are consistent |
| physical and chemical analysis | pH: 8.6 chemical oxygen demand (COD): 19.7 mg/l | | | | | ammonia-nitrogen ($NH_3$—N): 0.84 mg/l faecal coliform: 12567 pcs/L | | | moderate pollution | |

TABLE 5

Test Example V

| Test Method | Distribution number of tested fishes in each zone | | | | | Indicator light situation | | | Test result | |
| --- | --- | --- | --- | --- | --- | --- | --- | --- | --- | --- |
| | Zone I | Zone II | Zone III | Zone IV | Dead | Slight pollution warning lamp | Moderate pollution warning lamp | heavy pollution warning lamp | | |
| biological detection | 8 | 82 | 10 | 0 | 0 | ✓ | ○ | ○ | slight pollution | The test results are consistent |

TABLE 5-continued

Test Example V

| Test Method | Distribution number of tested fishes in each zone | | | | | Indicator light situation | | | Test result |
|---|---|---|---|---|---|---|---|---|---|
| | Zone I | Zone II | Zone III | Zone IV | Dead | Slight pollution warning lamp | Moderate pollution warning lamp | heavy pollution warning lamp | |
| physical and chemical analysis | pH: 6.3 chemical oxygen demand (COD): 15 mg/l | | | | | ammonia-nitrogen ($NH_3$—N): 0.6 mg/l faecal coliform: 7809 pcs/L | | | slight pollution |

In the test results, some fishes are dead, due to the fact that some indicator organisms were severely affected by the polluted water body when the water body to be tested was polluted, resulting in the death of the tested fishes. The biological detection method of the invention is consistent with the analysis result of the physical and chemical properties, which shows that the invention has very high accuracy and good practical application.

The above description is only one embodiment of the invention, not all the embodiments, and not intended to limit the invention. Any modification, equivalent replacement, improvement and the like made within the spirit and principle of the invention shall fall within the protection scope of the invention.

What is claimed is:

1. A biological water-quality detection method using an obstructive multi-module biological water-quality detection device, comprising: an obstructive multi-module biological water-quality detection device and a biological water-quality detection method, wherein said obstructive multi-module biological water-quality detection device includes a water-quality testing device, said water-quality testing device includes a testing water tank (1) and three obstruction units, an inlet gate (22) is installed at one end of said testing water tank (1), and an outlet gate (21) is installed at the other end, said three obstruction units are arranged at the first, second and third sections inside the testing water tank (1), respectively, the distances from the first, second and third sections to the inlet gate (22) increase in sequence, each obstruction unit includes an obstruction index-generating device and a counting device, the obstruction levels of the obstruction index-generating devices at the first, second, and third sections to the indicator organisms increases in sequence, said counting device is used to count the indicator organisms passing through said section, said water-quality testing device further includes an obstruction index-selecting device used to select each obstruction index-generating device, the obstruction index-selecting device includes a selection water tank (30), a pushing unit placed at one end of said selection water tank (30), and an obstruction-comparing unit and a monitoring unit that are placed at the other end of the said selection water tank (30), said pushing unit is used to push the liquid in said selection water tank (30) toward the obstruction unit, said obstruction-comparing unit includes a separating plate, said separating plate forms an obstruction section with four identical separated areas at said other end of said selection water tank (30), and each separated area is used to install one or more kinds of obstruction index-generating devices, a water inlet (34) is installed at one end of the selection water tank (30), a water outlet (38) is installed on the other end, said monitoring unit is used to monitor the indicator organisms' behavior at said obstruction section, wherein said method includes the following steps:

S1: selecting an indicator organism, and selecting and installing the obstruction index-generating device required in each obstruction unit in the testing water tank (1), in S1, where selecting the obstruction index-generating device required in each obstruction unit specially includes the following sub steps S1a-S1d:

S1a: establishing a single obstruction index, where said single obstruction index includes various single obstruction indexes, said single obstruction index can generate one or more kinds of obstruction levels, said single obstruction index includes a flash, a bubble curtain, a jet vortex, a temperature, or a sound, and establishing an indicator organism library, S1b: selecting one indicator organism from said indicator organism library, and selecting at least three kinds of valid single obstruction levels from said single obstruction index database, S1c: determining the obstruction index-generating device in the three obstruction units of said testing water tank (1) according to at least three kinds of valid single obstruction levels selected in S1b and S1d: installing an obstruction index-generating device at each section of said testing water tank (1) to generate said valid synthetical obstruction level combination, S2: injecting pollution-free water into the testing water tank (1), arranging a blocking net (41) between the inlet gate (22) and the obstruction unit at the first section, and placing the selected indicator organism between the blocking net (41) and the inlet gate (22), adapting the selected indicator organism to the environment for m minutes, m≥10, S3: starting each obstruction index-generating device in the testing water tank (1), removing the blocking net so that the water body to be tested flows into the testing water tank (1) through the inlet gate (22), S4: determining the water-quality of the water body to be tested according to the count changes of the counting devices inside the three obstruction units.

2. The biological water-quality detection method according to claim 1, wherein the obstruction index-generating device at the first section is used to generate a green single flash with frequency of 80-85 times/min, the obstruction index-generating device at the second section is used to generate a bubble curtain with air supply of 40-45 L/min, the obstruction index-generating device at the second section is used to generate a jet vortex with jet velocity of 1-1.1 m/s and a green single flash with frequency of 80-85 times/min.

3. The biological water-quality detection method according to claim 1, wherein each obstruction unit further includes a warning device corresponding to and connected to said counting device, said obstruction index-generating device includes one or more combinations of a flashing light-generating device, a bubble curtain-generating device, a jet vortex-generating device, a temperature-controlling device, a sound-generating device.

4. The biological water-quality detection method according to claim 1, wherein said testing water tank (1) further includes a water-guiding pipe (4) connected to said inlet gate (22) and a water inlet (3) of the testing water tank connected to said water-guiding pipe (4).

5. The biological water-quality detection method according to claim 4, wherein said pushing unit includes a pushing motor (31), a connecting chain rod (32) and a pushing plate (33), said pushing motor (31) drives said pushing plate (33) through said connecting chain rod (32) to push the liquid in the water tank (30) to said other end.

6. The biological water-quality detection method according to claim 4, wherein said monitoring unit includes two camera devices (39), and the two camera devices (39) are located on both sides of the obstruction section (36).

7. The biological water-quality detection method according to claim 1, wherein in S4,
in the case that the count of said counting device at the first section is less than 2/3 of the indicator organisms, the water-quality is normal,
in the case that the count of said counting device at the first section is not less than 2/3 of the indicator organisms and the count of said counting device at the second section is less than 2/3 of the indicator organisms, the water-quality is slightly polluted,
in the case that the count of said counting device at the second section is not less than 2/3 of the indicator organisms and the count of said counting device at the third section is less than 2/3 of the indicator organisms, the water-quality is moderately polluted,
in the case that the count of said counting device at the third section is not less than 2/3 of the indicator organisms, the water-quality is heavily polluted.

8. The biological water-quality detection method according to claim 1, wherein,
a method for selecting valid single obstruction levels comprises the following steps:
selecting the obstruction level corresponding to one obstruction level from said single obstruction index database, and installing the single obstruction index-generating device capable of generating the corresponding obstruction level in the second, third, and fourth separated areas of said obstruction-comparing unit, respectively, no obstruction index-generating device in the first separated area,
filling said selection water tank (30) with non-polluted water where indicator organisms are placed, pushing all the indicator organisms into said obstruction section by said pushing unit, counting the indicator organisms in each separated area by said monitoring unit,
marking the total number of selected indicator organisms as N, marking the number of the indicator organisms in the first to fourth separated areas as $N_a$, $N_b$, $N_c$, $N_d$, respectively, when $$N_a \geq \frac{2}{3}N,$$

the obstruction level corresponding to the selected single obstruction index having an obstructive effect on the indicator organism, which is called the valid single obstruction level, otherwise the invalid single obstruction level, having to select the obstruction level corresponding to the single obstruction index and make a judgement, if all the obstruction level of all the single obstruction indexes in said single obstruction index database are an invalid single obstruction level for the selected indicator organism, replacing the selected indicator organism so as to select a valid single obstruction level.

9. The biological water-quality detection method according to claim 1, wherein,
where the step S1c comprises the following sub steps:
making three kinds of synthetical obstruction levels, where each synthetical obstruction level is any one or a combination of more of the above at least three kinds of valid single obstruction levels, installing the obstruction index-generating device generating said three kinds of synthetical obstruction levels in the second, third, and fourth separated areas of said obstruction section, respectively, no obstruction index-generating device in the first separated area,
filling the selection water tank (30) with non-polluted water where indicator organisms are placed, pushing all the indicator organisms finally selected in S12 into the obstruction section by the pushing unit, counting the indicator organisms in each separated area by the monitoring unit,
when $N_a$, $N_b$, $N_c$, $N_d$ meets the following condition, judging that the selected three kinds of synthetical obstruction level combination is a valid synthetical obstruction level combination, otherwise an invalid synthetical obstruction level combination, having to repeat making new three kinds of synthetical obstruction level combination so as to finally select a valid synthetical obstruction level combination:

$$N_a = \frac{2}{3}N \pm 0.1N, \ N_b = \frac{2}{9}N \pm 0.07N, \ N_c = \frac{1}{12}N \pm 0.05N, \ N_d = \frac{1}{36}N \pm 0.03N,$$

* * * * *